United States Patent
Ramsauer

(10) Patent No.: US 7,548,605 B2
(45) Date of Patent: *Jun. 16, 2009

(54) MEDICAL IMAGING APPARATUS

(75) Inventor: Martin Ramsauer, Pyrbaum (DE)

(73) Assignee: Siemens Aktiengesellschaft, Munich (DE)

( * ) Notice: Subject to any disclaimer, the term of this patent is extended or adjusted under 35 U.S.C. 154(b) by 220 days.

This patent is subject to a terminal disclaimer.

(21) Appl. No.: 11/632,155

(22) PCT Filed: Jul. 5, 2005

(86) PCT No.: PCT/EP2005/053260

§ 371 (c)(1),
(2), (4) Date: Jan. 10, 2007

(87) PCT Pub. No.: WO2006/005719

PCT Pub. Date: Jan. 19, 2006

(65) Prior Publication Data

US 2008/0069299 A1 Mar. 20, 2008

(30) Foreign Application Priority Data

Jul. 15, 2004 (DE) .................. 10 2004 034 240

(51) Int. Cl.
*A61B 6/04* (2006.01)
(52) U.S. Cl. ....................................... 378/37
(58) Field of Classification Search .............. 378/19, 378/37, 98.8, 62, 167, 189
See application file for complete search history.

(56) References Cited

U.S. PATENT DOCUMENTS

| 5,579,366 A | 11/1996 | Doebert et al. ............ 378/189 |
| 6,102,866 A | 8/2000 | Nields et al. ............... 600/461 |
| 2003/0030721 A1 | 2/2003 | Nyholm ........................ 348/36 |
| 2004/0120453 A1 | 6/2004 | Vafi et al. ....................... 378/19 |
| 2007/0189447 A1* | 8/2007 | Holler et al. .................. 378/37 |

FOREIGN PATENT DOCUMENTS

| DE | 690 00 148 T2 | 10/1990 |
| EP | 0 776 126 A1 | 5/1997 |
| GB | 0776126 | 5/1997 |

OTHER PUBLICATIONS

International Search Report and translation of the PCT Written Opinion dated Nov. 17, 2005.
German Office Action for DE 10 2004 034 240.7-35 dated Mar. 14, 2005 and English translation.

* cited by examiner

*Primary Examiner*—Courtney Thomas
(74) *Attorney, Agent, or Firm*—Brinks, Hofer, Gilson & Lione

(57) ABSTRACT

A medical imaging apparatus is disclosed, which is configurable for generating mammographic images. The apparatus includes a radiation source for emitting a test radiation, a first device for receiving the test radiation, and a test area for placing a test object. The test area is located between the radiation source and the first receiving device in a beam path of the test radiation. The first receiving device supports a sensor for receiving the test radiation. The first receiving device can support at least one additional device and has at least one interface in order to provide a detachable electrical and, optionally, a mechanical connection to the at least one additional device.

15 Claims, 4 Drawing Sheets

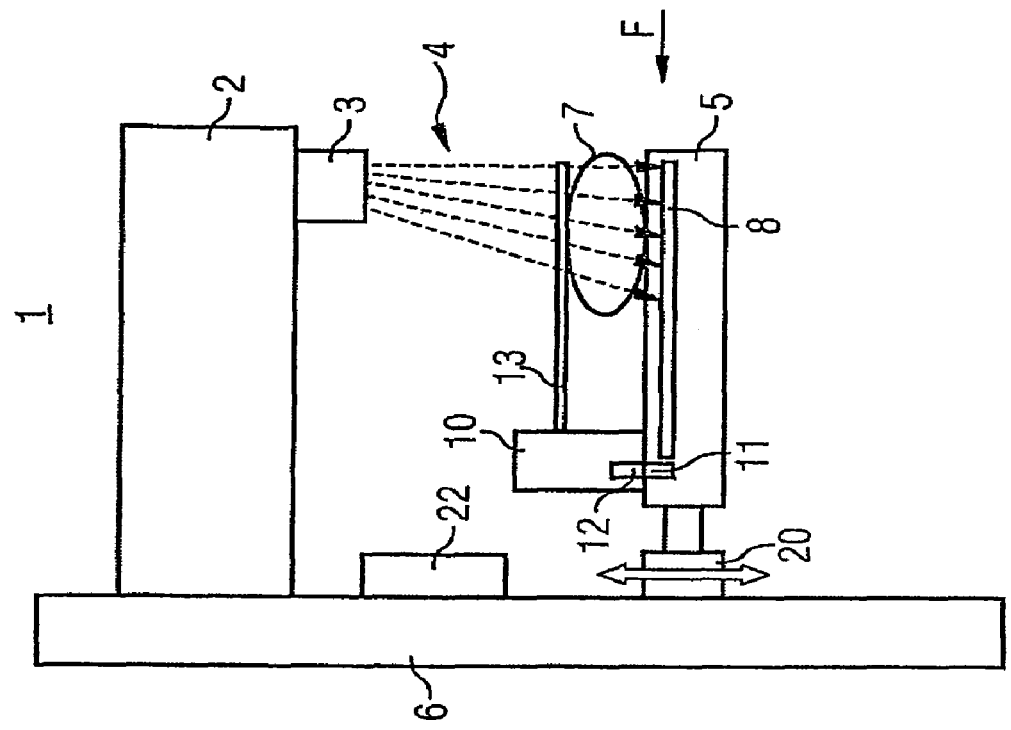
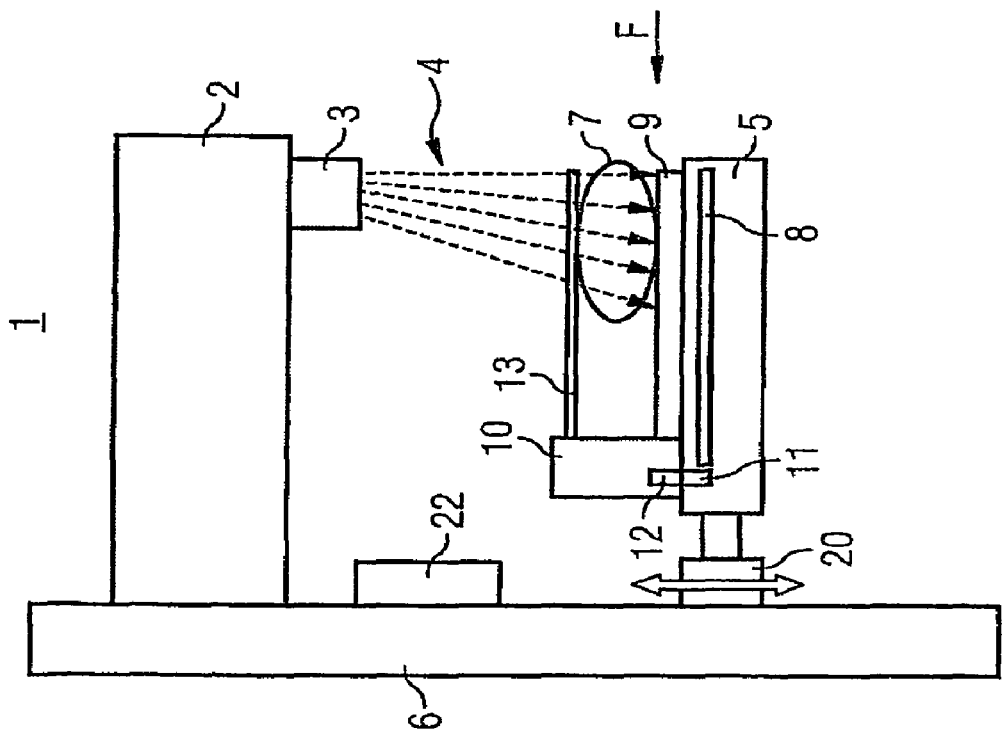

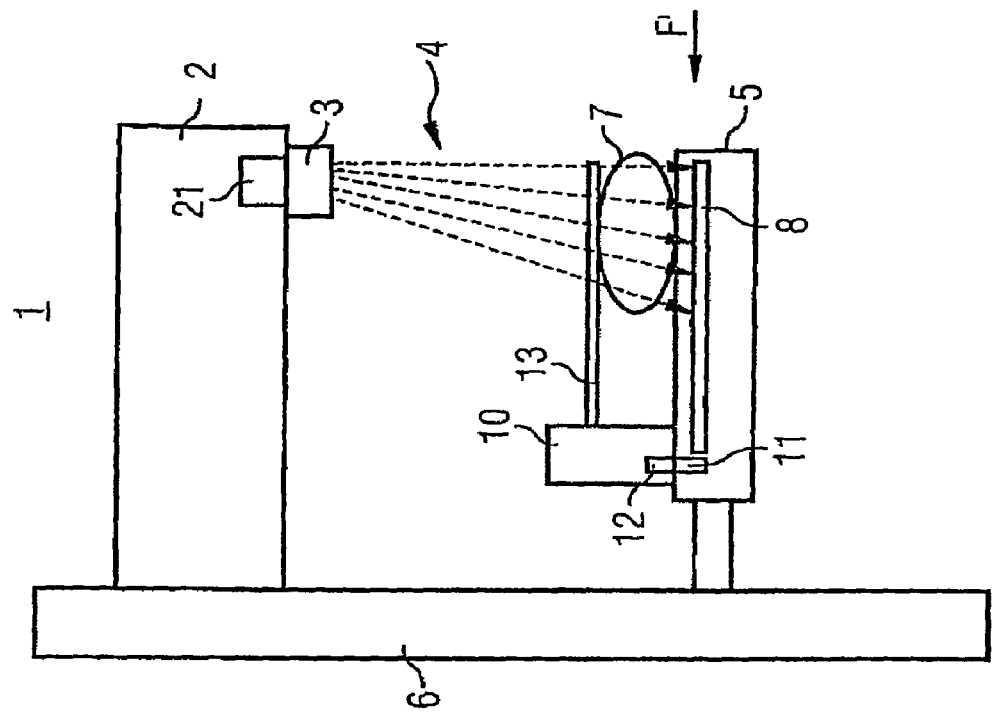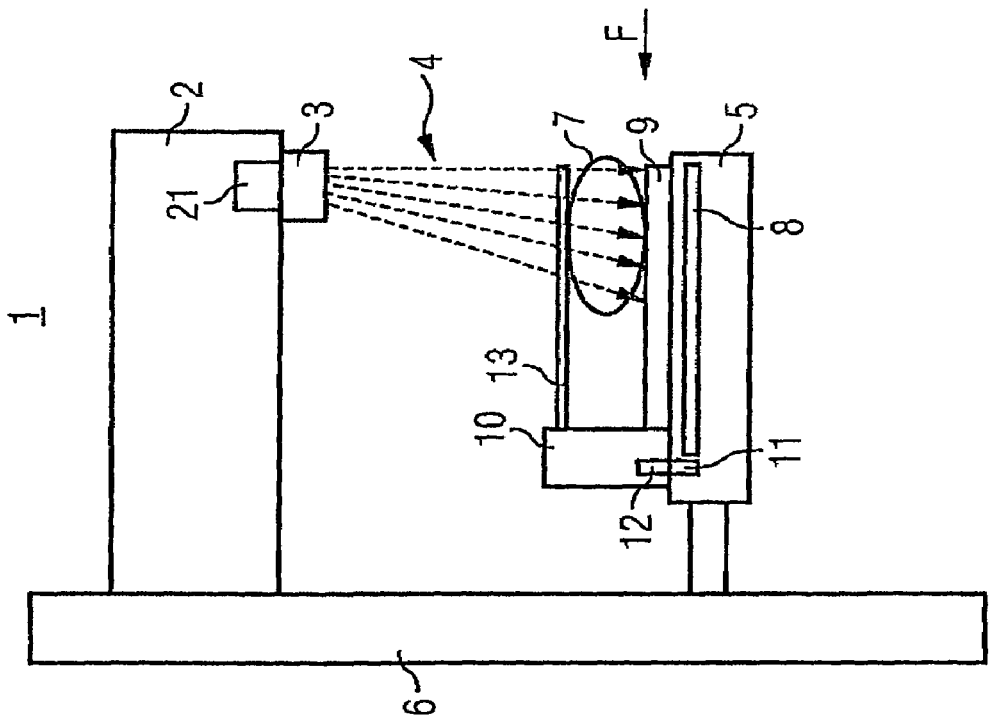

MEDICAL IMAGING APPARATUS

RELATED APPLICATIONS

The present application is a National Stage application of PCT Application No. PCT/EP2005/053260, filed Jul. 7, 2005, designating the United States and claiming priority to German Patent Application No. 10 2004 034 240.7, filed on Jul. 11, 2005, each of which are incorporated by reference.

TECHNICAL FIELD

The present application relates to a medical imaging apparatus for obtaining mammographic images suitable for performing biopsies.

BACKGROUND

Mammography is an x-ray examination of the female breast carried out using medical imaging apparatuses for obtaining mammographic images. Such apparatuses usually have an x-ray radiation source. The female breast under examination is exposed to x-ray radiation in order to obtain a projection x-ray image on an x-ray film disposed in the beam path beneath said female breast. During the examination the female breast is usually held between two compression plates.

The advantage of using x-ray films is that they provide a relatively sophisticated and, at least in terms of outlay, relatively inexpensive solution, while at the same time allowing long-term archiving of an acquired projection x-ray image using this medium.

Another advantage of using x-ray films is that x-ray films have a very large receiving area of typically 18×24 cm or 24×30 cm and a relatively high local resolution of approximately 14 LP/mm (LP=linear pairs), making it possible to create a high-resolution complete recording of the female breast in a single test.

The disadvantage of using x-ray films is that the images are not available in real-time, as the film must first be developed.

Instead of x-ray film, which can be used only once, a known solution is to use charge-coupled-device (CCD) sensors which can replace the x-ray film in a mammography machine.

In order to facilitate conversion of the equipment, the CCD sensors often have the same shape as conventional x-ray film cassettes. Such CCD sensors can be easily inserted in an existing mount for x-ray film cassettes. CCD sensors are electronic components suitable for locally resolving radiation measurement, in particular x-ray radiation, and generally consist of an array of radiation-sensitive cells also known as pixels.

The advantage of using CCD sensors is that, on the one hand, modern CCD sensors have a resolution of 10-20 LP/mm which in some cases exceeds the resolution of x-ray films and that, on the other hand, the images can be immediately made available and digitally processed. Unlike x-ray films, CCD sensors are therefore suitable for obtaining real-time images (during a biopsy, for example).

The disadvantage of using CCD sensors is that known CCD sensors with the required high resolution have a receiving surface which is much smaller than the receiving surface of x-ray films. Therefore, high-resolution CCD sensors are currently only suitable for capturing detailed images of the female breast or for stereotactical biopsy.

Additionally, known in the context of FFDM (Full Field Digital Mammography) is the use of low-resolution digital detectors.

Although the digital detectors used for FFDM have a resolution of typically 5 to 10 LP per millimeter and therefore a lower resolution than x-ray films, receiving surfaces having a size similar to the size of the receiving surfaces of conventional x-ray films can be implemented. Using the FFDM detectors, it is therefore possible to create a complete image of the female breast with a single test.

Advantages of FFDM detectors are therefore that the images are available in real-time, can be digitally processed, and the receiving surfaces are relatively large. The disadvantage is the relatively low resolution.

As an alternative to high- or low-resolution CCD sensors for obtaining mammographic images, the use of digital luminescence radiography with storage foil technology is also known.

In order to be able to make a reliable diagnosis as to whether a lump discovered in the female breast during mammography is benign or malignant, the creation of mammographic images is generally insufficient. Rather, it is usually necessary to extract a tissue sample from the breast as part of a biopsy, the lump in question first being located using a medical imaging apparatus for obtaining mammographic images and a biopsy needle for removing a tissue sample being inserted in the breast with a manipulator attached to the apparatus. When using a digital sensor for the x-ray radiation, this takes place under continuous monitoring by the medical imaging apparatus. Using an FFDM sensor for this purpose is generally insufficient, as the resolution is too low to ensure that the biopsy needle has actually reached the suspicious lump. Such continuous monitoring by the medical imaging apparatus is not possible when using an x-ray film.

In order to be able to combine the advantages of, for example, an FFDM sensor with the advantage of x-ray film or of a high-resolution CCD sensor, medical imaging apparatuses for obtaining mammographic images are known which have two receiving surfaces for x-ray radiation. The manipulator is mounted on such an apparatus in some cases by a separate support independent of the receiving surfaces. In other cases the manipulator is disposed directly on a receiving surface.

A related art apparatus with two receiving surfaces and manipulator will now be described in greater detail with reference to FIG. 4. The apparatus 41 for obtaining mammographic images has a head 42 with a radiation source 43 for emitting x-ray radiation 44 and a receiving device support 45. Both the head 42 and the receiving device support 45 are supported by a supporting column 46 via a mount 54. The supporting column 46 can be free-standing or fixed to the floor or ceiling of a room.

The receiving device support 45 has a first receiving surface 48 in the form of a holder for x-ray films and a second receiving surface 49 in the form of a large-area low-resolution detector with approx. 5-10 LP/mm for FFDM images.

The x-ray film holder is designed such that it can also accommodate a high-resolution CCD sensor. The high-resolution CCD sensor can then be connected to a suitable processing device or to the apparatus 41 by a connecting line (not shown). CCD sensors of this kind currently only have a receiving surface area of approximately 50 mm×80 mm and are incorporated in a mount having the same dimensions as an x-ray film cassette.

The two receiving surfaces 48 and 49 mounted to the receiving device support 45 are disposed at right angles to one another and are supported by the mount 54. The two receiving surfaces 48 and 49 can be alternately rotated about an axis of rotation 50 to a test position with a motor in the receiving device support 45. The axis of rotation 50 makes an angle of about 45° with the beam path of the x-ray radiation 44 emitted by the x-ray source 43. Such a design of the mounting of the receiving surfaces is known as "flying wing".

The angle of about 45° between the axis of rotation 50 and beam path of the x-ray radiation 44 ensures, in conjunction with the receiving surfaces 48, 49 disposed at an angle of 90° to one another, that by swiveling the support 45 about the axis of rotation 50, one of the receiving surfaces 48 outside the beam path can be disposed essentially parallel to the beam path and the other receiving surface 49 inside the beam path can be disposed essentially perpendicular to the beam path of the x-ray radiation 44.

In the beam path between a receiving surface 48 or 49 in the test position and the radiation source 43, a test area for disposing a test object 47 (for example, a female breast) is provided.

A biopsy unit 52 is supported by the receiving surface 49 disposed inside the beam path substantially perpendicular to the beam path of the x-ray radiation 44.

The biopsy unit 52 is suitable for taking tissue samples from the female breast 47 and supports a compression plate 53.

Alternatively, however, it is possible for the compression plate 53 to be supported and moved not by the biopsy unit 52 but by a compression device 51 of the medical imaging apparatus 41. In this case, the element 53 is a device for positioning and guiding a biopsy needle.

In addition, currently known biopsy units often incorporate a stage (not shown in FIG. 4) into which a film cassette or CCD sensor can be inserted.

By vertical movement of the compression plate 53 by the biopsy unit 52 or the compression device 51, it is possible to compress and hold the female breast 47 in the test area between the compression plate 53 and the receiving surface 48 or 49 in the test position.

As the compression plate 53 is disposed in the beam path of the x-ray radiation, it is a radiation-transparent material.

The disadvantage of the known apparatus is that, due to the projecting swiveling motion of the receiving surfaces 48 and 49, it has a high space requirement. In addition, manufacturing a correspondingly rotatable mechanical connection to the relevant receiving surfaces 48, 49 with the precision required in medical engineering is very demanding technically and therefore expensive.

Another disadvantage of the known design is that the head 42 incorporating the radiation source 43 and the receiving device support 45 are supported by a common mount 54. This complicates the design of the apparatus shown in FIG. 4, as the head 42 with the radiation source 43 must be electronically and mechanically decoupled from the rotary motion of the receiving device support 45. A further disadvantage is that an electrical connection to the second receiving surface 49 is generally provided with a separate cable which obstructs the swiveling motion of the receiving device support 45 and can easily be accidentally loosened.

SUMMARY

A medical imaging apparatus is described, including a radiation source for emitting a test radiation, a first receiving device for receiving the test radiation emitted by the radiation source, and a test area for placing a test object, the test area being disposed in a beam path of the test radiation between radiation source and the first receiving device. The first receiving device may support a first receiving sensor for receiving the test radiation. According to the invention, the first receiving device is designed to support at least one additional device and has at least one first interface in order to provide a detachable electrical connection to at least one other interface of the at least one additional device.

As the first receiving device is designed to support at least one additional device and has a first interface in order to provide a detachable electrical connection to at least one other interface of the at least one additional device, it is possible, to use a biopsy unit and/or an alternative receiving device for test radiation as the additional device on an optional basis.

In order to reliably prevent the at least one additional device supported by the first receiving device from falling off and/or ensure that the at least one additional device is supported by the first receiving device at a specified location, the at least one additional device is preferably detachably mounted to the first receiving device. Such a mechanical connection can preferably also be provided via the electrical interfaces.

The at least one additional device may be a second receiving device providable above the first receiving device and having a second receiving sensor for the test radiation.

The apparatus can therefore be easily and quickly modified for connecting alternative receiving devices for the test radiation. No projecting swiveling motion is required for this purpose. This also simplifies the electrical and mechanical connection to the first receiving device, as the connection can be fixed. As the second receiving device can be disposed above the first receiving surface of the first receiving device, the second receiving device is in the beam path of the test radiation. Horizontal adjustment of the position of the second receiving device may be unnecessary. In order to focus the test radiation emitted by the radiation source on the first or second receiving sensor, the medical imaging apparatus additionally has an adjusting device which changes the position of the first receiving device such that the distance between the radiation source and the first or second receiving sensor is constant. The adjustment may be carried out automatically.

Alternatively, or additionally, if the radiation source has a focusing device, the focusing device is used for adjusting the focal plane for the test radiation to the relevant distance between the radiation source and the first or the second receiving sensor. The adjustment may be carried out automatically.

The test radiation emitted by the radiation source is an x-ray radiation.

The receiving sensor of the second receiving device may be a solid-state detector for x-ray radiation, such as a CCD sensor. The receiving sensor of the first receiving device may be, for example, a digital detector for x-ray radiation, an x-ray film or a luminescence radiography foil.

An additional device type is, for example, a manipulator for manipulating a test object disposed in the test area or a biopsy unit for taking a tissue sample.

A plurality of additional devices may be simultaneously supported by the first receiving device and variably connectable to one another using intermediate interfaces and to the first receiving device using a common interface.

As the additional devices are connected to one another using intermediate interfaces and to the first receiving device using a single interface, the number of interfaces to be provided at the first receiving device can be minimized. This reduces the hygiene problems associated with interfaces generally, as interfaces tend to be difficult to clean.

The additional devices may have carbon-fiber housings, as such housings are substantially transparent to the test radiation beams normally used in medical engineering, have high stability, and can be easily cleaned, and therefore meet hygiene requirements.

The first receiving device may have a surface against which the test object may be placed, so that a test object can be supported by the first receiving device in addition to the at least one additional device. A separate support for the test object may not therefore be required.

To ensure that the surface available for a test object is not unnecessarily limited by the at least one additional device supported by the first receiving device, at least one of the additional devices may have a surface for placing the test object.

The medical imaging apparatus may be configured for obtaining mammographic images.

BRIEF DESCRIPTION OF THE DRAWINGS

FIGS. 1A, 1B show a schematic side view of a medical imaging apparatus for obtaining mammographic images according to a first example;

FIGS. 2A, 2B show a schematic side view of a medical imaging apparatus for obtaining mammographic images according to a second example;

DETAILED DESCRIPTION

Figure 3A:
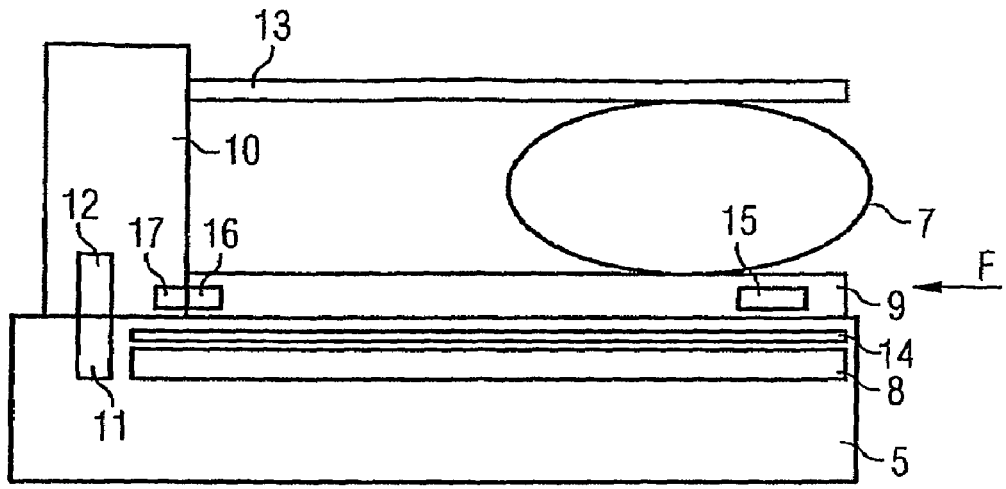
FIGS. 3A, 3B, 3C show a schematic cross section through various configurations and uses of the first receiving device.

In the following, the examples are described in detail with reference to the attached drawings. In the drawings, identical reference signs mark identical components, or components with the same functions, in the various views.

FIGS. 1A and 1B and 2A and 2B show a schematic side view of a medical imaging apparatus for obtaining mammographic images The apparatus 1 has a radiation source 3 supported by a head 2 for emitting test radiation, such as an x-ray radiation 4. The head 2 is supported by a supporting column 6. Below the radiation source 3 there is provided a first receiving device 5 for receiving the x-ray radiation 4 emitted by the radiation source 3.

The first receiving device 5 is supported by the supporting column 6. In this example, a housing of the first receiving device 5 is made of carbon fiber. Alternatively, however, the housing of the first receiving device 5 can be made of another material such as plastic, the material being substantially transparent to the test radiation.

Between the first receiving device 5 and the radiation source 3, a test area for disposing a test object 7, in this example a female breast, is provided in the beam path of the x-ray radiation 4.

The first receiving device 5 supports a first receiving sensor 8 for receiving the x-ray radiation 4. In this example, shown in FIGS. 1A and 1B, the first receiving sensor 8 may accommodate x-ray film cassettes containing x-ray film or another type of x-ray sensor. Alternatively, however, the first receiving sensor 8 can also accommodate a holder for luminescence radiography foils.

In the second example shown in FIGS. 2A and 2B, the first receiving sensor 8 may be a large-area, low-resolution, solid-state detector for x-ray radiation for creating FFDM (Full Field Digital Mammography) images.

The first receiving device 5 supports a manipulator 10. The manipulator 10 is detachably mounted to the first receiving device 5 by a quick-release connection system not specifically shown in the figures. In this case, the manipulator 10 is designed to take tissue samples from the female breast 7. Alternatively, the manipulator can manipulate the test object 7 in some other way.

A detachable electrical and mechanical connection to a first additional interface 12 of the manipulator 10 is provided by a first interface 11 of the first receiving device 5.

It may therefore be possible for the manipulator 10 to be controlled by the medical imaging apparatus 1 through the electrical connection established by the first interface 11 and the first additional interface 12. The connection, as shown in FIGS. 1A, 1B, 2A, 2B may be established using a direct plug-in contact. This may obviate the need for an external connection cable.

Alternatively, or additionally to the core arrangement of a quick-release connection system, a detachable mechanical connection between manipulator 10 and receiving device 5 may also be established using the first interface 11 and the first additional interface 12.

The manipulator 10 may be a compression plate 13 that may be moved vertically by the manipulator 10. As the compression plate 13 is disposed in the beam path of the x-ray radiation 4, a material that is substantially transparent to x-ray radiation is used, such as a plastic; in this example, PLEXIGLAS (Polymethyl methacrylate (PMMA)).

Alternatively, the compression plate 13 may be directly mounted to the medical imaging apparatus 1 and can be actuated by the same using a compression device 22. The element 13, supported by the manipulator 10 can be, for example, a device for positioning and guiding a biopsy needle.

In another aspect, the first receiving device 5 in FIGS. 1A and 2A supports a second receiving device 9. There is a detachable electrical and mechanical connection between the first receiving device 5 and the second receiving device 9, as shown in FIG. 3.

As shown in FIGS. 1A and 1B, and 2A and 2B, the first and second receiving devices 5 and 9 respectively are disposed one above the other and substantially parallel to one another and substantially perpendicular to the beam path of the x-ray radiation 4.

By the optional disposition of the second receiving device 9, it is therefore possible to take mammographic images using different receiving devices 5, 9, which may have different sensors, and therefore different test methods.

As the second receiving device 9 may be disposed above the first receiving device 5 and supported by same, the arrangement is simple mechanically, and a "flying wing" may not be needed, while nevertheless enabling different test methods to be performed.

As shown in FIGS. 1A, 1B, 2A and 2B, a surface of the first or second receiving device 5, 9 facing the x-ray source 3 serves both as the surface for placing the test object and as a lower compression surface for the test object (in this example, the female breast 7).

Disposing the second receiving device 9 above the first receiving device 5 results in a slight deviation from the focusing plane F of the x-ray radiation 4 emitted by the radiation source 3, as the distance between the sensor in the second receiving device 9 and the radiation source 3 is slightly less than the distance between the sensor in the first receiving device 5 and the radiation source 3. FIGS. 1 and 2 show two different examples accommodating the deviation from the original focusing plane F.

In FIGS. 1A, 1B, the first receiving device 5 is shown attached by a motor 20 to the supporting column 6 of the medical imaging apparatus 1. The motor 20 displaces the first receiving device 5 vertically along the supporting column 6. By vertically displacing the first receiving device 5 with respect to the radiation source 3 in this manner, the sensor of the second receiving device 9 or the sensor 8 of the first receiving device 5 is disposable in the focusing plane F. This positionability optically focuses the x-ray beams 4 during an examination.

As shown in FIGS. 2A, 2B, the spatial position of the first receiving device 5 is fixed in a position with respect to the medical imaging apparatus 1 during the examination. The focusing plane F or F' of the x-ray radiation 4 emitted by the radiation source 3, is adjusted by a focusing device 21, provided in the head 2.

The focusing device 21, adjusts the focusing plane to substantially coincide with a sensor in the second receiving device 9 used as shown in FIG. 2A or to the first receiving sensor 8 of the first receiving device 5 as shown in FIG. 2B.

This adjustment focuses the x-ray radiation 4 on the desired sensor during an examination.

The focus adjustment may also be performed both by varying the distance between sensors of the receiving devices and the radiation source 3 and by varying the focusing plane by the focusing device 21.

In the first embodiment shown in FIG. 1 and in the second embodiment shown in FIG. 2, the adjustment of the position of the first receiving device 5 by the motor 20, or of the focusing plane F, F' by the focusing device 21, may be performed automatically.

For this purpose, the medical imaging apparatus 1 detects, using the first interface 11, whether the first receiving device 5 supports any additional receiving device and whether any such additional device is a second receiving device 9. The second receiving device 9 is automatically identified using the first interface 11, so that automatic adjustment is possible.

Figure 3B:
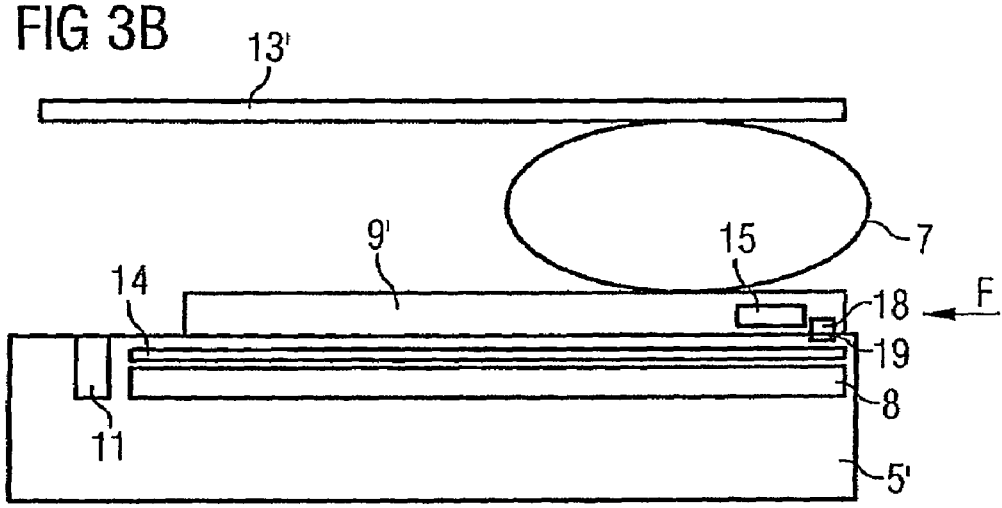
Figure 3C:
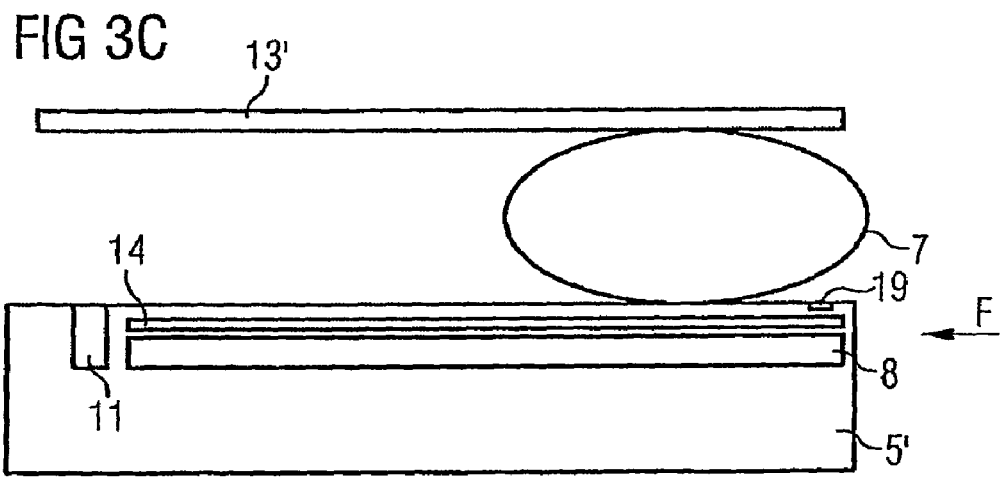
Figure 4:
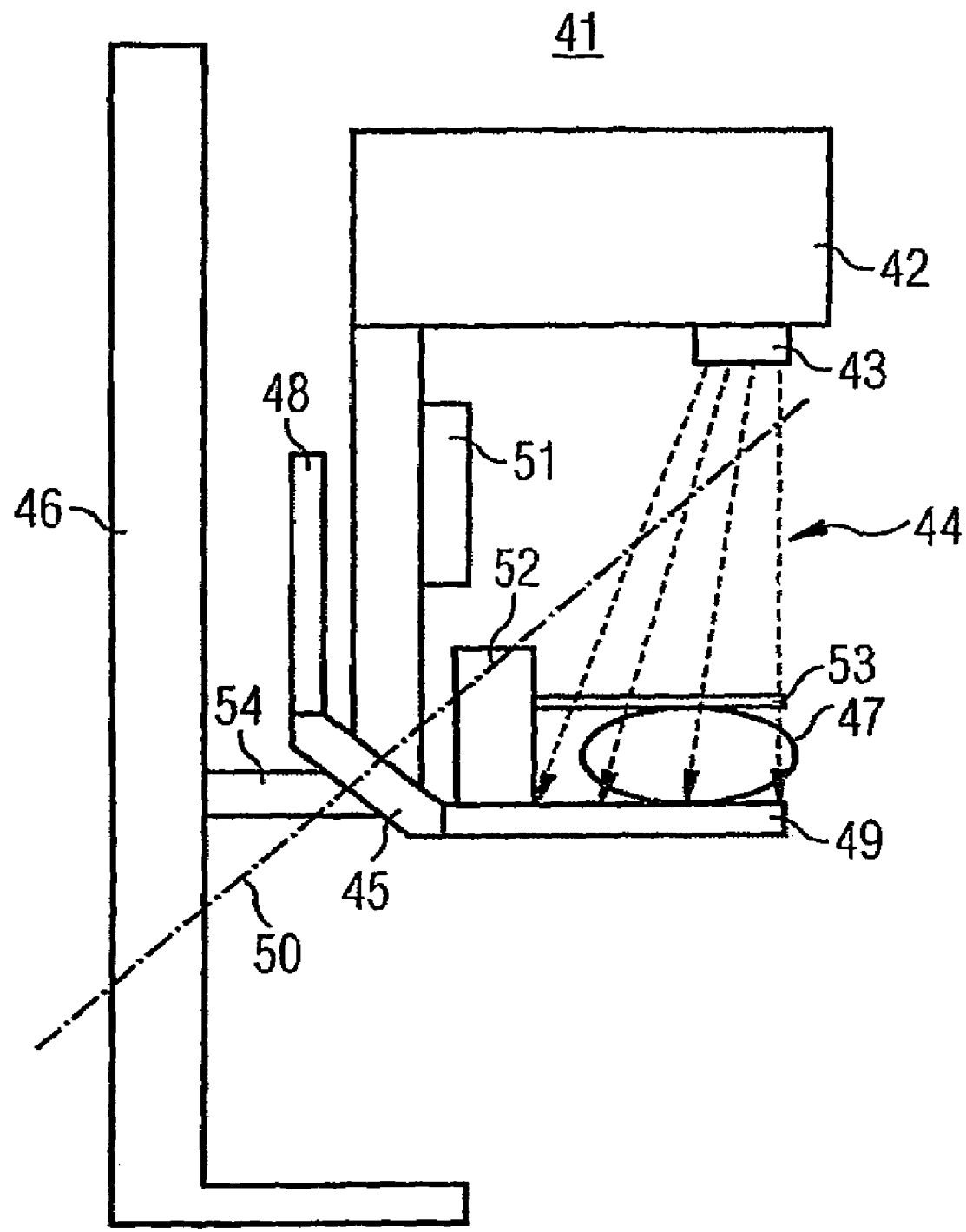
FIG. 4 schematically illustrates a medical imaging apparatus for obtaining mammographic images according to the prior art.

FIGS. 3A, 3B, 3C are schematic section views through different examples and uses of the first receiving device 5 or 5'. In FIG. 3A, the first receiving sensor 8 supported by the first receiving device 5 is an x-ray film cassette.

In FIGS. 3B and 3C, the first receiving sensor 8 supported by the first receiving device 5 is a digital detector for FFDM imaging.

In front of the support for x-ray film cassettes or the digital detector, a filter 14 is disposed. In this example, the filter 14 is a scatter grid adapted for use with x-ray films or the digital detector as appropriate.

In FIG. 3A, both a manipulator 10 with a compression plate 13 and a second receiving device 9 are supported by the first receiving device 5. The second receiving device 9 has a receiving sensor 15 for x-ray radiation 4. The receiving sensor 15 is a high-resolution CCD sensor for creating detailed images of the female breast 7. The receiving sensor 15 of the second receiving device 9, as part of the second receiving device 9, is disposed above the first receiving sensor 8 of the first receiving device 5.

In order to prevent uncontrolled displacement of the second receiving device 9, the second receiving device 9 is detachably mounted to the first receiving device 5 by means of a quick-release mechanism not shown in FIG. 3A.

With the motor 20 or focusing device 21, the focusing plane may automatically adjusted to coincide with the second receiving surface 15.

The second receiving device 9 has a first intermediate interface 16 by which the second receiving device 9 is electrically connected in a detachable manner to a second intermediate interface 17 of the manipulator 10.

A mechanical connection to the manipulator 10 may also be established using the first intermediate interface 16, thereby providing a detachable mechanical attachment of the second receiving device 9 to the first receiving device 5.

The manipulator 10 is electrically connected in a detachable manner to a first interface 11 of the first receiving device 5 by a first additional interface 12. The first additional interface 12 also serves in conjunction with the first interface 11, to mechanically attach the manipulator 10 to the first receiving device 5 in a detachable manner, and may obviate the need to provide another mechanical attachment of the manipulator 10 to the first receiving device 5.

As the manipulator 10 and the second receiving device 9 are connected to one another using intermediate interfaces 16 and 17, respectively, and to a common first interface 11 of the first receiving device 5 using a common first additional interface 12, an interface for both the manipulator 10 and the second receiving device 9 on the first receiving device 5 is used to make the connections.

As the manipulator 10 and the second receiving device 9 are connected to one another by intermediate interfaces 16, 17 and to the first receiving device 5 by a single interface 12, the number of interfaces to be provided on the first receiving device 5 is reduced. This reduces the hygiene problems associated with interfaces generally, as interfaces tend to be difficult to clean.

In FIG. 3B, only one second receiving device 9' is supported by the first receiving device 5'. A manipulator 10 is not provided and compression plate 13' is directly connected to the medical imaging apparatus 1, and is displaceable by same. To perform a biopsy, a manipulator would therefore is connected electrically and possible also mechanically to the first receiving device 5' using the first interface 11 (see FIG. 1A).

As shown in FIG. 3B, the first receiving device 5' has a first interface 11 and a second interface 19. The first interface 11 is not used and is therefore available for another additional device to be supported by the first receiving device 5'.

Using the second interface 19, both a detachable mechanical and a detachable electrical connection is established to a second additional interface 18 of the second receiving device 9'.

As the second receiving device 9' is locally attached using the connection between the second interface 19 of the first receiving device 5' and the second additional interface 18 of the second receiving device 19', no further measures need be taken for physically attaching the second receiving device 19' in this example. Additional fixing devices may therefore be dispensed with.

The medical imaging apparatus 1 is configured to be adjustable so that the focusing plane F for the x-ray radiation 4 coincides with the sensor receiving sensor 15 of the second receiving device 19 when required during the examination.

The second receiving devices 9 and 9' have a carbon-fiber housing allowing the x-ray beams 4 to penetrate to the receiving sensor 15.

FIG. 3C shows a further aspect of using the first receiving device 5' of the inventive medical imaging apparatus for obtaining mammographic images.

The first receiving device 5' has a first interface 11 and a second interface 19. Using the first and/or second interface 11 and 19 respectively an electrical and/or mechanical connection to an additional device supportable by the first receiving device 5' is possible.

In the configuration shown here, however, the first receiving device 5' does not support an additional device, so that the test object 7 is placed in direct contact with first receiving device 5'.

The medical imaging device 1 is configured such that, in the example shown in FIG. 3C, the focusing plane F corresponds to the first receiving surface 8 of the first receiving device 5'.

As shown in FIGS. 3A, 3B and 3C, both the first receiving device 5 or 5' and the second receiving device 9 or 9' have a surface for placing the test object 7.

In the foregoing, the simultaneous disposition of only two additional devices on the first receiving device has been described. However, the first receiving device can also simultaneously support more than two additional devices. For this purpose more than two interfaces can also be provided on the first receiving device. Alternatively, more than two additional devices can also be interconnected via more than two intermediate interfaces.

In addition to using a manipulator for the biopsy and using a second receiving device it is also possible to dispose another additional device on the first receiving device. Instead of a high-resolution CCD sensor, for example another suitable solid-state detector for the relevant test radiation can also be used as the receiving sensor of the second receiving device.

Although only a few exemplary embodiments of this invention have been described in detail above, those skilled in the art will readily appreciate that many modifications are possible in the exemplary embodiments without materially departing from the novel teachings and advantages of the invention. Accordingly, all such modifications are intended to be included within the scope of this invention as defined in the following claims.

The invention claimed is:

1. A medical imaging apparatus, comprising:
   a radiation source;
   a first receiving device operable to have a first sensor for receiving test radiation emitted by the radiation source; and
   a test area for placing a test object disposed in a beam path of the test radiation,
   wherein the first receiving device is designed to support at least one additional device and has a first interface operable to provide a detachable electrical connection to an interface of the at least one additional device.

2. The medical imaging apparatus as in claim 1, wherein the additional device is detachably mountable to the first receiving device.

3. The medical imaging apparatus as in claim 1, wherein the additional device is a second receiving device disposable above the first sensor of the first receiving device and having a second sensor for the test radiation.

4. The medical imaging apparatus as in 3, further comprising an adjusting device adapted to vary a position of the first receiving device such that a distance between the radiation source and either one of the first sensor of the first receiving device or the second sensor of the second receiving device is a same constant distance.

5. The medical imaging apparatus as in claim 3, wherein the radiation source has a focusing device to adjust a focusing plane for the test radiation to a distance between the radiation source and either one of the first sensor of the first receiving device or the second sensor of the second receiving device.

6. The medical imaging apparatus as in claim 1, wherein the test radiation emitted by the radiation source is an x-ray radiation.

7. The medical imaging apparatus as in claim 1, wherein a second sensor of the second receiving device is a solid-state detector for x-ray radiation.

8. The medical imaging apparatus as in 7, wherein the solid-state detector is a charge-coupled-device (CCD) sensor.

9. The medical imaging apparatus as in claim 6, wherein the first sensor of the first receiving device is one of a digital detector, an x-ray film, or a luminescence radiography foil.

10. The medical imaging apparatus as in claim 2, wherein the additional device is a manipulator for manipulating a test object disposed in the test area.

11. The medical imaging apparatus as in claim 10, wherein a plurality of additional devices supported by the first receiving device are connectable to one another by intermediate interfaces and to the first receiving device by the first interface.

12. The medical imaging apparatus as in claim 1, wherein the at least one additional device has a housing made of carbon fiber.

13. The medical imaging apparatus as in claim 1, the first receiving device has a surface on which the test object is placeable.

14. The medical imaging apparatus as in claim 2, wherein the at least one of the additional devices has a surface on which the test object is placeable.

15. The medical imaging apparatus as in claim 1, wherein the medical imaging apparatus is configurable to obtaining mammographic images.

* * * * *